United States Patent
Sembo et al.

(10) Patent No.: US 6,200,973 B1
(45) Date of Patent: Mar. 13, 2001

(54) COMPOSITION FOR EXTERMINATION OF HARMFUL ARTHROPODS

(75) Inventors: Satoshi Sembo; Satoshi Nakamura, both of Takarazuka (JP)

(73) Assignee: Sumitomo Chemical Company, Limited, Osaka-fu (JP)

( * ) Notice: Subject to any disclaimer, the term of this patent is extended or adjusted under 35 U.S.C. 154(b) by 0 days.

(21) Appl. No.: 09/356,509

(22) Filed: Jul. 19, 1999

(30) Foreign Application Priority Data

Aug. 5, 1998 (JP) .................................................. 10-221586
Jan. 18, 1999 (JP) .................................................. 11-009095

(51) Int. Cl.⁷ .......................... A01N 43/08; A01N 43/40; H61K 31/535
(52) U.S. Cl. ........................ 514/229.2; 514/345; 514/471
(58) Field of Search ................................ 514/471, 229.2, 514/345

(56) References Cited

U.S. PATENT DOCUMENTS 5,532,365  7/1996  Kodaka et al. .
5,852,012  12/1998  Maienfisch et al. .

FOREIGN PATENT DOCUMENTS 8217609  8/1996  (JP) .
WO9617520A1  6/1996  (WO) .
WO9740692A1  11/1997  (WO) .

OTHER PUBLICATIONS

Tomlin, The Pesticide Manual Incorporating the Agrochemicals Handbook 10ᵗʰEd. (1995) pp. 887 & 888.*

* cited by examiner

*Primary Examiner*—Allen J. Robinson
(74) *Attorney, Agent, or Firm*—Birch, Stewart, Kolasch, & Birch, LLP

(57) ABSTRACT

A composition for the extermination of harmful arthropods, which contains at least one compound selected from 1-(tetrahydrofuran-3-yl)methyl-3-methyl-2-nitroguanidine and 3-[(2-chloro-5-thiazolyl)methyl]-5-methyl-4-nitroiminotetrahydro-1,3,5-oxadiazine, and pyriproxyfen, as active ingredients, exhibits remarkable synergism and therefore has excellent extermination effects against various harmful arthropods by their application in smaller amounts.

13 Claims, No Drawings

COMPOSITION FOR EXTERMINATION OF HARMFUL ARTHROPODS

FIELD OF THE INVENTION

The present invention relates to a composition for the extermination of harmful arthropods.

BACKGROUND OF THE INVENTION

Various types of agents for the extermination of harmful arthropods have been used so far. In some cases of application, however, it cannot be said that they exhibit satisfactory effects.

SUMMARY OF THE INVENTION

Under these circumstances, the present inventors have extensively studied many compositions for the extermination of harmful arthropods. As a result, they have found that the combined use of at least one compound selected from 1-(tetrahydrofuran-3-yl)methyl-3-methyl-2-nitroguanidine and 3-[(2-chloro-5-thiazolyl)methyl]-5-methyl-4-nitroiminotetrahydro-1,3,5-oxa-diazine with pyriproxyfen makes it possible to exhibit remarkable synergism and therefore gives excellent extermination effects against various harmful arthropods by their application in smaller amounts, thereby completing the present invention.

Thus, the present invention provides a composition for the extermination of harmful arthropods (hereinafter referred to as the present composition), characterized in that it comprises at least one compound (hereinafter referred to as the nitroimino compound) selected from 1-(tetrahydrofuran-3-yl)methyl-3-methyl-2-nitroguanidine and 3-[(2-chloro-5-thiazolyl)methyl]-5-methyl-4-nitroiminotetrahydro-1, 3,5-oxadiazine, and pyriproxyfen, as active ingredients.

DETAILED DESCRIPTION OF THE INVENTION

The nitroimino compound used in the present invention is known to have control activity against various pests in the field of agriculture and disclosed in U.S. Pat. Nos. 5,532,365 and 5,852,012. On the other hand, pyriproxyfen is a compound commercially available as the active ingredient of pesticides for domestic prevention of epidemics and for agriculture.

The mixing ratio of nitroimino compound to pyriproxyfen used in the present composition as expressed by the "nitroimino compound/pyriproxyfen (weight ratio)" is usually not higher than 1000/1, preferably not higher than 100/1, and more preferably not higher than 10/1, but usually not lower than 1/10, preferably not lower than 1/5, and more preferably not lower than 1/1. That is, the mixing ratio of nitroimino compound to pyriproxyfen is generally in the range of from 1000:1 to 1:10, preferably from 100:1 to 1:10.

The harmful arthropods which can be exterminated by the present composition may include, for example, those of the following orders, families and genera:

Isopoda: *Oniscus asellus, Armadillidium vulgare, Porcellio scaber*, etc.

Diplopoda: *Blanilus guttulatus* etc.

Chilopoda: *Geophilus carpophagus*, Scutigera spp., Scolopendra subspinipes, Thereunema spp., etc.

Symphyla: *Scutigerella immaculata* etc.

Thysanura: *Ctenolepisma villosa, Lepisma saccharina*, etc.

Psocoptera: *Trogium pulsatorium* etc.

Collembola: *Onychiurus armatus* etc.

Ipostera: Mastotermitidae; Termopsidae such as Zootermopsis, Archotermopsis, Hodotermopsis (e.g., *Hodotermopsis japonica*) and Porotetmes; Kalotermitidae such as Kalotermes, Neotermes (e.g., *Neotermes koshuensis*), Cryptotermes (eg., *Cryptotermes domesticus*), Incisitermes (e.g, ancisitermes minor) and Glyptotermes (e.g, *Glyptotermes satsumaensis, Glyptotermes nakajimai, Glyptotermes fuscus*); Hodotermitidae such as Hodotermes, Microhodotermes and Anacanthotermes; Rhinotermitidae such as Reticulitermes (e g., *Retitulitermes speratus, Retitulitermes kanmonensis, Retitulitermes flaviceps, Retitulitermes miyatakei*), Heterotermes, Coptotermes (eg, *Coptotermes formosnus*) and Schedolinotermes; Serritermitidae; Termitidae such as Amitermes, Drepanotermes, Hopitalitermes, Trinervitermes, Macrotermes, Odontotermes (e.g., *Odontotermes formosanus*), Microtermes, Nasutitermes (e.g., *Nasutitermes takasagoensis*), Pericapritermes (e.g., *Pericapritermes nitobei*) and Anoplotermes, etc:

Dictyoptera: *Blatta orientalis, Periplaneta americana, Periplaneta fuliginosa, Leucophaea maderae, Blattella germanica*, etc.

Orthoptera: Gryllotalpa spp., *Acheta domesticus, Teleogryllus emma, Locusta migratoria, Melanoplus differentialis, Schistocerca gregaria*, etc.

Dermaptera: *Labidura riparia, Forficula auricularia*, etc.

Mallophaga: *Trichodectes spp., Tromenopon spp., Bovicola spp., Felicola spp.*, etc.

Thysanoptera: *Frankliniella intonsa, Thrips tabaci, Thrips palmi*, etc.

Heteroptera: Nezara spp., Eurygaster spp., *Dysdercus intermedius, Nezara antennata, Cletus punetiger*, etc.

Homoptera: *Aleurocanthus spiniferus, Bemisia tabaci, Bemisia argentifoili, Trialeurodes vaporariorum, Aphis gossypii, Brevocoryne brassicae, Cryptomyzus ribis, Aphis fabae, Macrosiphum euphorbiae, Myzus persicae, Phorodon humuli*, Empoasca spp., *Nephotettix cincticeps, Lecanium corni, Saissetia oleae, Laodelphax striatellus, Nilaparvata lugens, Aonidiella aurantii; Aspidiotus hederae*, Pseudococcus spp., Psylla spp., *Phylloxera vastatrix*, etc.

Lepiodoptera: *Pectinophora gossypiella, Lithocolletis blancardella, Plutella xylostella, Malacosoma neustria, Euproctis suhflava, Lymantria dispar, Bucculatrix pyrivorella, Phyllocnistis citrella*, Agrotis spp., Euxoa spp., *Earias insulana*, Heliothis spp., *Spodoptera exigua, Spodoptera litura*, Spodoptera spp., *Mamestra brassicae, Trichoplusia ni, Carpocapsa pomonella*, Pieris spp., Chilo spp., *Pyrausta nubilalis, Ephestia kuehniella, Galleria mellonella, Tineola hisselliella, Tinea translucens, Homona magnanima, Tortrix viridana*, etc.

Coleoptera: *Anobium punctatum, Rhizopertha dominica, Acanthoscelides obtectus, Agelastica alni, Leptinotarsa decemlineata, Phaedon cochleariae*, Diabrotica spp., *Psylliodes angusticollis, Phyllotreta striolata*, Epilachna spp., Atomaria spp., *Oryzaephilus surinamensis*, Anthonomus spp., Sitophilus spp., *Otiorhynchussulcatus, Cosmopolitessordidus, Ceuthorhyncidius albosuturalis, Hypera postica*, Dermestes spp., Togoderma spp., *Attagenus unicolor*, Lyctridae (e.g., *Lyctus dentatum, Lyctus planicollis, Lyctus sinensis, Lyctus linearis, Lyctus hrunneus, Lyctus*

*africanus*), *Meligethes aeneus*, Ptinus spp., *Gibbium psylloides*, Tribolium spp., *Tenebrio molitor*, Agriotes spp., *Melolontha mololontha*; Scolytidae such as Xylehorus and Scolytoplatypus; Ceramhycidae such as Monochamus, Hylotrupes, Hesperophanus, Chlorophorus, Palaeocallidium, Semanotus, Purpuricenus and Stromatium; Platypodidae such as Crossotarsus and Platypus; Bostrychidae such as Dinoderus, Bostrychus and Sinoderus ; Anohiidae such as Ernohius, Anohium, Xyletinus, Xestobium, Ptilinus, Nicobium and Ptilineurus; Buprestidae, etc.

Hymenoptera: Diprion spp., Hoplocapma spp., Lasius spp., Formica japonica, Vespa spp.; Siricidae such as Urocerus and Sirex, etc.

Diptera: Aedes spp., Anopheles spp., Culex spp., *Drosophila melanogaster, Musca domestica*, Fannia spp., Calliphora spp., Lucilia spp., Chrysomya spp., Cuterehra spp., Gastrophilus spp., Stomoxys spp., Oestrus spp., Hypoderma spp., Tabanus spp., *Bibio hortulanus, Pegomyia hyoscyami, Ceratitis capitata, Dacus dorsalis, Tipula paludosa*, Simulium spp., Eusimulium spp., Phlebotomus spp., Culicoides spp., Chrysops spp., Haematopota spp., Braula spp., Morellia spp., Wohlfahrtia spp., Sarcophaga spp., Lipoptena spp., Melophagus spp., Muscina spp., etc.

Arachnida: *Scorpio maurus, Latrodectus mactans*, Chiracanthium spp., etc.

Acarina: *Acarus siro*, Eriophyes spp., *Chelacaropsis moorei*, Dermatophagoides spp., Tarsonemus spp., *Bryobia praetiosa*, Panonychus spp., Tetranychus spp., Acarapis spp., Cheyletiella spp., Myobia spp., Listrophorus spp., Trophagus spp., Cytodides spp., Laminosioptes spp., etc.

The present composition, although it may be composed merely of the nitroimino compound and pyriproxyfen, is usually used for practical applications as formulations which suitably contain solid carriers, liquid carriers, auxiliary agents and other additives. The formulations may be in the form of emulsifiable concentrates, oil sprays, flowables, solutions, dusts, wettable powders, granules, paste preparations, foams, aerosol preparations, carbon dioxide gas preparations, tablets, sheet-shaped preparations, or resin preparations. At the time of application, a preferred form is suitably selected for the formulation.

The content of nitroimino compound and pyriproxyfen, although it may vary with the form of formulation, is usually 0.005% to 50% by weight in total.

These formulations can be obtained by any of the ordinary methods, for example, by mixing the nitroimino compound and pyriproxyfen with solid or liquid carriers, and adding, if necessary, other auxiliary agents such as emulsifiers and fixing agents, followed by further mixing, and subsequently forming the mixture into a desired form for some particular formulations. The carriers and auxiliary agents which can be used in the formulation may include, for example, the following materials:

The solid carrier may include, for example, natural or synthetic minerals such as clay, kaolin, talc, bentonite, sericite, quartz, sulfur, active carbon, calcium carbonate, diatomaceous earth, pumicite, calcite, sepiolite, dolomite, silica, alumina, vermiculite and perlite; fine granules of sawdust, corncobs, coconut shells and tobacco stems; gelatin, petrolatum, methylcellulose, lanolin, lard, and liquid petrolatum.

The liquid carrier may include, for example, aromatic or aliphatic hydrocarbons such as xylene, toluene, alkylnaphthalenes, phenylxylylethane, kerosine, light oil, hexane and cyclohexane; halogenated hydrocarbons such as chlorobenzene, dichloromethane, dichloroethane and trichloroethane; alcohols such as methanol, ethanol, isopropyl alcohol, butanol and hexanol; ethers such as diethyl ether, ethylene glycol dimethyl ether, tetrahydrofuran and dioxane; esters such as ethyl acetate and butyl acetate; ketones such as acetone, methyl ethyl ketone, methyl isobutyl ketone and cyclohexanone; nitriles such as acetonitrile and isobutyronitrile; sulfoxides such as dimethylsulfoxide; acid amides such as N,N-dimethylformamide and N,N-dimethylacetamide; vegetable oils such as soybean oil and cottonseed oil; essential oils such as orange oil, hyssop oil and lemon oil; and water.

The propellant which can be used in the foam, aerosol preparation or carbon dioxide gas preparation may include, for example, propane gas, butane gas, Freon gas, LPG ( liquefied petroleum gas), dimethyl ether, and carbon dioxide gas.

The base material which can be used in the resin preparation may include, for example, vinyl chloride polymers and polyurethane. These base materials may contain, if necessary, plasticizers such as phthalic acid esters (e.g., dimethyl phthalate, dioctyl phthalate), adipic acid esters and stearic acid. The resin preparation can be obtained by kneading the active ingredients in the base material with a conventional kneader, and then forming the mixture into a desired form using injection, extrusion, pressing or other molding techniques. If necessary, further molding, cutting and other additional steps can be used to make a resin preparation into plate, film, tape, net, cord or other forms. For example, the resin preparation can also be made into collars for animals, ear tags for animals, sheets, attractive cords, wrapping films, or garden poles.

The auxiliary agents may include, for example, nonionic emulsifiers such as polyoxyethylene fatty acid esters and polyoxyethylene fatty acid alcohol ethers; ionic emulsifiers such as alkylsulfonates, alkylsulfates and arylsulfonates; dispersing agents such as ligninsulfonates and methylcellulose; fixing agents such as carboxymethylcellulose, gum arabic, polyvinyl alcohol and polyvinyl acetate; and coloring agents such as iron oxide, titanium oxide, Prussian blue, alizarin dyes, azo dyes and phthalocyanine dyes.

The present composition may further contain synergistic agents such as PBO, S421, MGK264, IBTA and Synepirin 500.

The present composition is usually used by its application directly to harmful arthropods or indirectly to their habitats. The application amount when the present composition is used for domestic prevention of epidemics is, for example, about 0.001 to 10 mg/m$^3$ as the amount of active ingredients for the control of flies and mosquitoes in the house or about 0.001 to 100 mg/m$^2$ as the amount of active ingredients for the control of cockroaches and ants. The "amount of active ingredients" as used herein refers to the total amount of nitroimino compound and pyriproxyfen unless otherwise indicated.

For the control of wood-infesting pests, the present composition may be directly applied to these pests, but it is usually applied to their habitats, i.e., wood materials and soil. The application amount, although it may vary with the kinds of harmful arthropods to be controlled, forms of formulations, application places, application methods and other factors, is generally about 0.1 to 10000 mg/m$^2$ as the amount of active ingredients.

The present composition when used for agriculture is usually applied in a ratio of about 1 to 1000 g/ha, preferably about 10 to 300 g/ha, as the amount of active ingredients. If the present composition is formulated into emulsifiable concentrates, wettable powders, flowables or similar forms, the application concentration is usually 1 to 1000 ppm, preferably 10 to 200 ppm, for the active ingredients. In the case of granules, dusts or similar forms, the present composition is usually applied as such. These formulations and their aqueous dilutions may be used either for foliar application on plants such as crop plants to be protected against harmful arthropods or for soil application to control the harmful arthropods inhabiting the soil of cropland. The present composition can also be applied in the form of sheets, cords or other processed resin preparations, for example, by directly winding them around crop plants, disposing them in the vicinity of crop plants, or laying them on the surface of soil at the base of crop plants.

EXAMPLES

The present invention will be further illustrated by the following Examples; however, it is understood that the present invention is not limited to these Examples.

Formulation Example 1

Five parts by weight of 3-[(2-chloro-5-thiazolyl)methyl]-5-methyl-4-nitroiminotetrahydro-1,3,5-oxadiazine, 10 parts by weight of pyriproxyfen, 8 parts by weight of polyoxyethylene alkyl aryl ether, 2 parts by weight of sodium alkylarylsulfonate, and 75 parts by weight of xylene were mixed to give an emulsifiable concentrate.

Test Example 1

For 1-(tetrahydrofuran-3-yl)methyl-3-methyl-2-nitroguanidine (hereinafter referred to as compound A) and pyriproxyfen (hereinafter referred to as compound B), a 0.1% (w/v) solution in ethanol was each prepared and then diluted with water to give each 1 ppm aqueous solution of compound A or B. Both solutions were mixed in prescribed proportions to give test solutions with a ratio of compound A/B concentrations (in ppm) of 1.0/0 (compound A only), 0.99/0.01, 0.9/0.1, 0.8/0.2, 0.7/0.3, 0.5/0.5, and 0/1.0 (compound B only) (seven test solutions in total). To 50 g of medium for flies (a mixture of bran and powdered feed for animals) was added 100 ml of a test solution, followed by mixing, which was put into a 650-ml plastic cup. In a nylon net cage (width, 21 cm; depth, 28 cm; and height, 21 cm) were placed water, feed (skim milk: granulated sugar=2:1), and two cups containing the medium treated with the test solution as described above. Thirty 4-day-old larvae of the housefly (CSMA strain) were put into one of the two medium-containing cups. Twenty adults of the housefly (CSMA strain, sex ratio=1) were further set free in this cage. The number of houseflies surviving in the cage was then observed after 1, 2 and 8 days, and the accumulated number was recorded.

For reference, the same test was carried out, except that a medium treated with water was used.

The rate of control, the expected rate of control, and the synergism index were determined by the following equations for calculation:

Rate of control (%)=(C−T)÷C×100 where C is the accumulated number of surviving adult flies in the reference cage and T is the accumulated number of surviving adult flies in the treated cage.

Expected rate of control (%)=P×mixing ratio of compound A+Q× mixing ratio of compound B where P is the rate of control by compound A only (1 ppm) and Q is the rate of control by compound B only (1 ppm).

Synergism index=rate of control÷expected rate of control×100

The experiment was carried out in duplicate. The results are shown in Table 1.

TABLE 1

| Compound A/B | | Accumulated number of surviving adult flies | Rate of control (%) | Expected rate of control (%) | Synergism index |
|---|---|---|---|---|---|
| Mixing ratio | Conc. (ppm) | | | | |
| 100:0 | 1.0/0 | 25.0 | 51.0 | — | — |
| 99:1 | 0.99/0.01 | 15.5 | 69.6 | 50.8 | 137 |
| 90:10 | 0.90/0.10 | 10.0 | 80.4 | 49.2 | 163 |
| 80:20 | 0.80/0.20 | 12.0 | 76.5 | 47.5 | 161 |
| 70:30 | 0.70/0.30 | 21.0 | 58.8 | 45.7 | 129 |
| 50:50 | 0.50/0.50 | 25.0 | 51.0 | 42.2 | 121 |
| 0:100 | 0/1.0 | 34.0 | 33.3 | — | — |
| reference (blank) | | 51.0 | — | — | — |

Test Example 2

The same experiment as described in Test Example 1 was carried out, except that compound A was changed to 3-[(2-chloro-5-thiazolyl)methyl]-5-methyl-4-nitroiminotetrahydro-1,3,5-oxadiazine (hereinafter referred to as compound C), five test solutions with a ratio of compound C/B concentrations (in ppm) of 1.0/0 (compound C only), 0.9/0.1, 0.7/0.3, 0.5/0.5, 0/1.0 (compound B only) were used, and the experiment was carried out once. For reference, the same results as obtained in Test Example 1 were used. The results are shown in Table 2.

The rate of control and the expected rate of control were determined by the equations for calculation as defined in Test Example 1, except that the values of compound A were changed to those of compound C.

TABLE 2

| Compound C/B | | Accumulated number of surviving adult flies | Rate of control (%) | Expected rate of control (%) | Synergism index |
|---|---|---|---|---|---|
| Mixing ratio | Conc. (ppm) | | | | |
| 100:0 | 1.0/0 | 20.0 | 60.8 | — | — |
| 90:10 | 0.90/0.10 | 5.0 | 90.2 | 58.1 | 155 |
| 70:30 | 0.70/0.30 | 12.0 | 76.5 | 52.6 | 145 |
| 50:50 | 0.50/0.50 | 17.0 | 66.7 | 47.1 | 142 |
| 0:100 | 0/1.0 | 34.0 | 33.3 | — | — |
| reference (blank) | | — | — | — | — |

Comparative Test Example 1

The same experiment as described in Test Example 2 was carried out, except that compound B was changed to methoprene (hereinafter referred to as comparative compound 1). For reference, the same results as obtained in Test Example 1 were used. The results are shown in Table 3.

The rate of control and the expected rate of control were determined by the equations for calculation as defined in Test Example 1, except that the values of compound B was changed to those of comparative compound 1.

TABLE 3

| Compound A/ Comparative Compound 1 | | Accumulated number of surviving | Rate of control | Expected rate of control | Synergism |
|---|---|---|---|---|---|
| Mixing ratio | Conc. (ppm) | adult flies | (%) | (%) | index |
| 100:0 | 1.0/0 | 25.0 | 51.0 | — | — |
| 90:10 | 0.90/0.10 | 26.0 | 49.0 | 48.3 | 101 |
| 70:30 | 0.70/0.30 | 29.0 | 43.1 | 42.8 | 101 |
| 50:50 | 0.50/0.50 | 35.0 | 31.4 | 37.3 | 84 |
| 0:100 | 0/1.0 | 39.0 | 23.5 | — | — |
| reference (blank) | | — | — | — | — |

Test Example 3

Cabbage seedlings planted in plastic cups were placed in a net cage containing many living silver leaf whiteflies for 24 hours, so that many silver leaf whiteflies became parasitic on the cabbage seedlings. An emulsifiable concentrate of compound A (prepared by mixing 5 parts by weight of compound A, 9 parts by weight of Sorpol 3005X (from Toho Chemical Industries, Co., Ltd.), 11 parts by weight of xylene, and 10 parts by weight of DMF), an emulsifiable concentrate of compound B (trade name: Lano EC; from Sumitomo Chemical Company, Limited), or a mixture of these emulsifiable concentrates of compounds A and B were each diluted in their prescribed amounts with water, and then sprayed over the cabbage seedlings with spray guns. The number of silver leaf whiteflies (i.e., the total number of adults and larvae) surviving on the cabbage seedlings was examined just before and after 10 days from the treatment.

For reference, the same test was carried out, except that a cabbage seedling treated with water was used.

The rate of control and the expected rate of control were determined by the following equations for calculation:

$$\text{Rate of control (\%)} = 100 \times \{1 - (T + T_0) \div (C \div C_0)\}$$

where T is the number of surviving whiteflies in the treated cage after 10 days from the treatment, $T_0$ is the number of surviving whiteflies in the treated cage just before the treatment, C is the number of surviving whiteflies in the reference case after 10 days from the treatment, and $C_0$ is the number of surviving whiteflies in the reference cage just before the treatment.

$$\text{Expected rate of control (\%)} = P + (100 - P) \times Q \div 100$$

where P is the rate of control by compound A only (in 50 ppm) and Q is the rate of control by compound B only (in 50 ppm).

The experiment was carried out once. The results are shown in Table 4.

TABLE 4

| Compound A/B | | Number of whiteflies surviving just before treatment | Number of whiteflies surviving after 10 days from treatment | Rate of control (%) | Expected rate of control (%) | Synergism index |
|---|---|---|---|---|---|---|
| Mixing ratio | Conc. (ppm) | | | | | |
| 1:0 | 50/0 | 92 | 128 | 25.9 | — | — |
| 1:1 | 50/50 | 99 | 0 | 100 | 76.9 | 130 |
| 0:1 | 0/50 | 111 | 65 | 68.8 | — | — |
| reference (blank) | | 81 | 152 | 0 | — | — |

Test Example 4

The same experiment as described in Test Example 3 was carried out, except that compound A was changed to compound C. For compound B only and for reference, the same results as obtained in Test Example 3 were used. The results are shown in Table 6.

The rate of control and the expected rate of control were determined by the equations for calculation as defined in Test Example 3, except that the values of compound A were changed to those of compound C.

TABLE 5

| Compound C/B | | Number of whiteflies surviving just before treatment | Number of whiteflies surviving after 10 days from treatment | Rate of control (%) | Expected rate of control (%) | Synergism index |
|---|---|---|---|---|---|---|
| Mixing ratio | Conc. (ppm) | | | | | |
| 1:0 | 50/0 | 88 | 98 | 40.7 | — | — |
| 1:1 | 50/50 | 96 | 0 | 100 | 81.5 | 123 |
| 0:1 | 0/50 | 111 | 65 | 68.8 | — | — |
| reference (blank) | | 81 | 152 | 0 | — | — |

What is claimed is:

1. A composition for the extermination of harmful arthropods, which comprises synergistically effective amounts of pyriproxyfen, and at least one compound selected from 1-(tetrahydrofuran-3-yl)methyl-3-methyl-2-nitroguanidine and 3-((2-chloro-5-thiazolyl)methyl)-5-methyl-4-nitroiminotetrahydro-1,3,5-oxadiazine as active ingredients.

2. The composition according to claim 1, wherein the weight ratio of at least one compound selected from 1-(tetrahydrofuran-3-yl)methyl-3-methyl-2-nitroguanidine and 3-[(2-chloro-5-thiazolyl)methyl]-5-methyl-4-nitroiminotetrahydro-1,3,5-oxadiazine to pyriproxyfen is in the range of from 100:1 to 1:10.

3. The composition according to claim 1, wherein 1-(tetrahydrofuran-3-yl)methyl-3-methyl-2-nitroguanidine and pyriproxyfen are contained as active ingredients.

4. The composition according to claim 3, wherein the weight ratio of 1-(tetrahydrofuran-3-yl)methyl-3-methyl-2-nitroguanidine to pyriproxyfen is in the range of from 100:1 to 1:10.

5. The composition according to claim 3, wherein the weight ratio of 1-(tetrahydrofuran-3-yl)methyl-3-methyl-2-nitroguanidine to pyriproxyfen is in the range of from 99:1 to 1:1.

6. The composition according to claim 1, wherein 3-(2-chloro-5-thiazolyl)methyl)-5-methyl-4- nitroiminotetrahydro-1,3,5-oxadiazine and pyriproxyfen are contained as active ingredients.

7. The composition according to claim 6, wherein 3-(2-chloro-5-thiazolyl)methyl)-5-methyl-4-nitroiminotetrahydro-1,3,5-oxadiazine to pyriproxyfen is in the range of from 100:1 to 1:10.

8. The composition according to claim 6, wherein 3-(2-chloro-5-thiazolyl)methyl)-5-methyl-4-nitroiminotetrahydro-1,3,5-oxadiazine to pyriproxyfen is in the range of from 9:1 to 1:1.

9. A method for the control of harmful arthropods, which comprises treating harmful arthropods or their habitats with synergistically effective amounts of pyriproxyfen and at least one compound selected from 1-(tetrahydrofuran-3-yl)methyl-3-methyl-2-nitroguanidine and 3-(2-chloro-5-thiazolyl)methyl)-5-methyl-4-nitroiminotetrahydro-1,3,5-oxadiazine.

10. The method according to claim 9 wherein the weight ratio of at least one compound selected from 1-(tetrahydrofuran-3-yl)methyl-3-methyl-2-nitroguanidine and 3-[(2-chloro-5-thiazolyl)methyl]-5-methyl-4-nitroiminotetrahydro-1,3,5-oxadiazine to pyriproxyfen is in the range of from 100:1 to 1:10.

11. The method according to claim 9, wherein 1-(tetrahydrofuran-3-yl)methyl-3-methyl-2-nitroguanidine and pyriproxyfen are utilized.

12. The method according to claim 9, wherein 3-(2-chloro-5-thiazolyl)methyl)-5-methyl-4-nitroiminotetrahydro-1,3,5-oxadiazine and pyriproxyfen are utilized.

13. The method according to claim 9, wherein the arthropods are houseflies or whiteflies.

* * * * *